US00PP13726P29

(12) United States Plant Patent

Bunnik et al.

(10) Patent No.: US PP13,726 P2

(45) Date of Patent: Apr. 15, 2003

(54) VRIESEA PLANT NAMED 'DEPLARLY'

(75) Inventors: Jan Bunnik, Kudelstaart (NL); Siegfried Bunnik, Kudelstaart (NL)

(73) Assignee: Bunnik Vriesea's BV, Kudelstaart (NL)

( * ) Notice: Subject to any disclaimer, the term of this patent is extended or adjusted under 35 U.S.C. 154(b) by 0 days.

(21) Appl. No.: 09/963,946

(22) Filed: Sep. 27, 2001

(51) Int. Cl.[7] ..... A01H 5/00

(52) U.S. Cl. ..... Plt./370

(58) Field of Search ..... Plt./370

(56) References Cited

U.S. PATENT DOCUMENTS

PP10,368 P * 4/1998 Deroose ..... Plt./370

PP10,874 P * 5/1999 Deroose ..... Plt./370

* cited by examiner

*Primary Examiner*—Bruce R. Campell

*Assistant Examiner*—W C Haas

(74) *Attorney, Agent, or Firm*—Foley & Lardner

(57) ABSTRACT

A new and distinct Vriesea plant named 'Deplarly' characterized by red with yellow inflorescence toward the margins of the bracts, 32–35 cm in total height in a 11 cm pot; each inflorescence has about 9–10 branches, each about 8–12 cm long; branching starts very low on the stem; the branches are compact and are about 4.5–6.4 cm in width; abundant medium green foliage in a dense rosette; a thick stem about 10–14 mm in diameter; compact leaves about 20 cm long and 4–4.5 cm in width.

2 Drawing Sheets

LATIN NAME OF THE GENUS AND SPECIES OF THE PLANT CLAIMED

*Vriesea lindl.*

VARIETY DENOMINATION

Deplarly.

BACKGROUND OF THE INVENTION

The present invention relates to a new and distinct cultivar of Vriesea plant, botanically known as *Vriesea lindl.* hereinafter referred to by the cultivar name 'Deplarly'.

The new cultivar originated from a cross made in a controlled breeding program in Kudelstaart, The Netherlands. The female and male parents are unknown. 'Deplarly' was selected as a single plant from a group of plants of several lots of seedlings some 15 years ago. 'Deplarly' was discovered and selected by the joint inventors, Jan Bunnik and Siegfried Bunnik, as a single flowering plant within the progeny of the stated cross in a controlled environment in Kudelstaart, The Netherlands.

Asexual reproduction of the new cultivar by vegetative means, by tissue culture was first performed in 1996 in Belgium and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Deplarly', which in combination distinguish this Vriesea as a new and distinct cultivar:

1. The inflorescence is red with yellow toward the margins of the bracts, and is about 32–35 cm in total height in a 11 cm pot;
2. Each inflorescence has about 9–10 branches, each about 8–12 cm long;
3. Branching starts very low on the stem;
4. The branches are compact and are about 4.5 to 6.4 cm in width;
5. Abundant medium green foliage in a dense rosette;
6. A thick stem about 10–14 mm in diameter;
7. Compact leaves about 20 cm long and 4 to 4.5 cm in width.

'Deplarly' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Kudelstaart, The Netherlands under conditions which closely approximate those generally used in commercial practice.

Of the many commercial cultivars known to the present inventor, the most similar in comparison to 'Deplarly' is cultivar 'Tiffany' (unpatented). 'Deplarly' has shorter but slightly wider leaves which measure 14–16 cm in length and about 4 to 4.5 cm in width, whereas the leaves of 'Tiffany' measure 17–19 cm in length and about 3.5 to 4 cm in width. The color of the upper surface of the leaves of 'Deplarly' is RHS 137 A, and the under side is RHS 137 B. The leaves of 'Tiffany' are slightly darker. The leaves of 'Deplarly' are less susceptible to leaf spickling than the leaves of 'Tiffany'. The leaves of 'Tiffany' droop significantly more than the leaves of 'Deplarly'. The inflorescence of 'Deplarly' branches more bracts, about 9–10, than the inflorescence of 'Tiffany', which branches about 4–5. The inflorescence of 'Deplarly' starts producing branches at the bottom of the stem, contrary to inflorescence of 'Tiffany' which branches about 5–9 cm from the bottom of the stem. The shape of the branches also differ. The branch shape of 'Deplarly' is more compact with a flatter top than the branch shape of 'Tiffany'. The branches of 'Deplarly' are about 8–12 cm in length and 4.5–6.5 in width, whereas the branches of 'Tiffany' are about 11–13 cm in length and 4.5–5 cm in width. 'Deplarly' has red-brown, RHS 46 A, bracts with yellow-orange, closest to RHS 17 A) tips and the center bract has a large yellow-green spot, RHS 150 B. 'Tiffany' has mainly red bracts, RHS 45 A, with yellow-orange, closest to RHS 11 A tips, with a sharper transition to yellow than 'Deplarly'. The stem color of 'Deplarly' is RHS 46 A, and the stem color of 'Tiffany' is RHS 46 B.

BRIEF DESCRIPTION OF THE DRAWING

The accompanying photographic drawings show typical inflorescence and foliage of 'Deplarly', with colors being as true as possible with illustrations of this type.

The first drawing, with 'Deplarly' on the left, shows the difference in leaf size when compared to 'Tiffany' on the right.

The second drawing, with the inflorescence of 'Deplarly' on the left, shows 'Deplarly's' many branches in comparison to 'Tiffany' on the right.

DETAILED BOTANICAL DESCRIPTION

The following observations, measurements and values describe a 21 month old plant of the new cultivar as grown in Kudelstaart, The Netherlands under conditions which closely approximate those generally used in commercial practice. 'Deplarly' is grown in a commercial greenhouse under 21 degrees Celsius day and night. No artifical lighting or photoperiodic treatments are conducted but 'Deplarly' is forced into flowery by adding acethylene. Highest temperature resistance is 40 degrees Celsius, the lowest is 5 degrees Celsius. The following fertilizer is added: 1 part nitrogen, 0.5 parts phosfor, 3 parts Kalium and 0.2 parts magnesium. From the start of tissue culture it takes five years to produce a commercial plant. The amount of time needed to produce a flower depends on the amount of acethylene is added. The flowers have a tenability of up to six months depending on the environment they are grown and kept in.

Color references are made to The Royal Horticultural Society Colour Chart (R.H.S.), except where general colors of ordinary significance are used. Color values were taken under daylight conditions at approximately noon in Rijswijk, The Netherlands.

Parentage:
- *Male parent.*—Seedling of unknown parentage.
- *Female parent.*—Seedling of unknown parentage.

Propagation: Tissue culture.

PLANT

General appearance and form:
- *Height.*—Approximately 32 to 35 cm in total height when grown in a 11 cm pot.
- *Width.*—Approximately 30 to 35 cm in diameter when grown in a 11 cm pot.
- *Shape.*—Basal rosette.
- *Plant vigor.*—Good.
- *Crop time.*—23 months: 14 months from tissue culture to young plant plus 9 months to maturity.
- *Flowering season.*—Year round.
- *Winter hardiness.*—5 degrees Celsius.
- *Lastingness of the individual bloom.*—Approximately 6 months.
- *Rooting habit.*—Freely branching.
- *Rooting time.*—6 weeks from tissue culture.
- *Fragrance.*—None.

Foliage:
- *Overall shape of leaf.*—Ensiform and bending down, up to 20 cm long and 4–4.5 cm wide. Base: Strap like around central axis. Tip: Cuspidate and bending down.
- *Margin.*—Entire.
- *Texture.*—Glabrous.
- *Quantity.*—25–32.
- *Main color of upper surface.*—Mature leaf: Green, slightly darker but closest to RHS 137 A. Immature leaf: Green, slightly darker but closest to RHS 137 A.
- *Main color of lower surface.*—Mature leaf: Green, RHS 137 B. Immature leaf: Green, RHS 137 B.
- *Venation color.*—Upper surface: Slightly visible (very fine), same color as leaf color. Lower surface: Slightly visible (very fine), same color as leaf color.
- *Size.*—Length: Up to 20 cm long for a mature leaf. Width: Approximately 4–4.5 cm wide for a mature leaf.
- *Leaf base shape.*—Strap like around central axis.
- *Leaf apex shape.*—Cuspidate and bending down.

Inflorescence: Scape bracts are oriented erect about 32 to 35 cm in height, glabrous: 9 to 10 branches.
- *Flowers.*—1 flower per floral bract, typical for the genus Vriesea; flowering is normally in progression from base to tip of scape or bracts; color is yellow RHS 11 A with green sepal tips RHS 144 A.
- *Flower longevity.*—Up to 6 months depending on environmental factors.
- *Corolla.*—Form: Long and narrow, petals and sepals fused at the base around the ovary. Shape: Ligulate. Average Number of Corollas: More than 100. Size: 3.5–4 cm. Petal Number: 3. Petal Shape: Ligulate. Petal Color: Upper surface: Green, RHS 144 A. Lower surface: Yellow, RHS 11 A. Sepal number: 3. Sepal Shape: Ligulate. Sepal color: Upper surface: Yellow, RHS 11 A. Lower surface: Yellow, RHS 11 A. Floral Bract Color: Red to orange-yellow; lowest bract red RHS 46A at the base, to yellow-orange RHS 16A at the top. Floral Bract Size: Length 3–5 cm; width 1–5 cm. Floral Bract Apex Shape: Asymmetrical. Floral Bract Margin: Entire.
- *Stem.*—Average length: 28–30 cm. Average diameter: 6–8 mm. Color: White. Internode length: 1.2–2 cm.

Reproductive organs:
- *Stamen.*—4–4.5 cm long and 0.9 mm in diameter. Number: 5–7 per flower. Color: Light yellow RHS 6 D with yellow anthers, RHS 11 A.
- *Seeds.*—None produced.
- *Fruit.*—None produced.
- *Anthers.*—6 mm. Color: Yellow, RHS 11 A, with dark brown to black stripes, RHS 200 A to RHS 202 A. Shape: Long, narrow with rounded tips on both sides.
- *Pollen.*—Color: Yellow, RHS 11 A.
- *Style.*—Length: 4–4.5 cm long. Color: Yellow, RHS 11 A, turning green toward the stigma, RHS 145 A.
- *Stigma.*—Shape: 3 small heart shaped parts attached to a center. Size: 3 mm in width. Color: Green, RHS 145 B.

*Ovary.*—Conical 7–8 mm in length and 2–2.5 mm in diameter. Color: Yellow, RHS 14 A.

Disease resistance: Better resistance against Pineapple mite than Vriesa cultivar 'Tiffany'.

I claim:

1. A new and distinct Vriesea plant named 'Deplarly', substantially as illustrated and described herein.

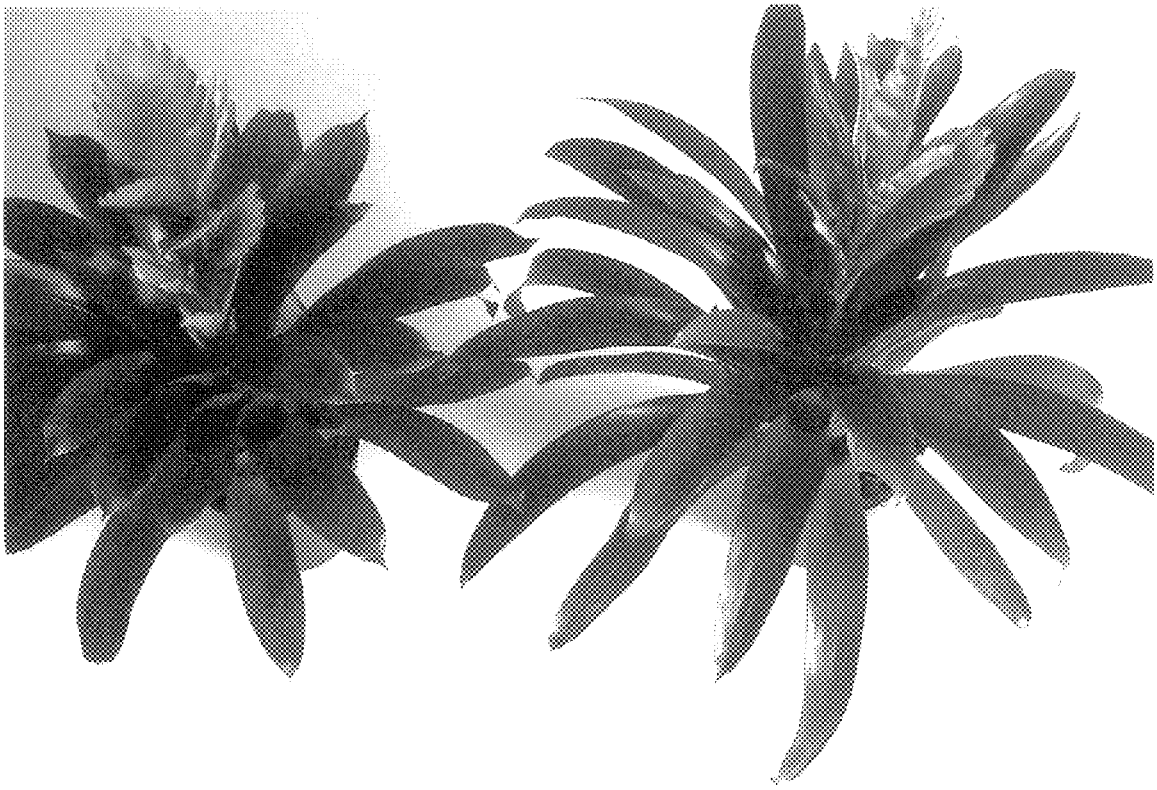

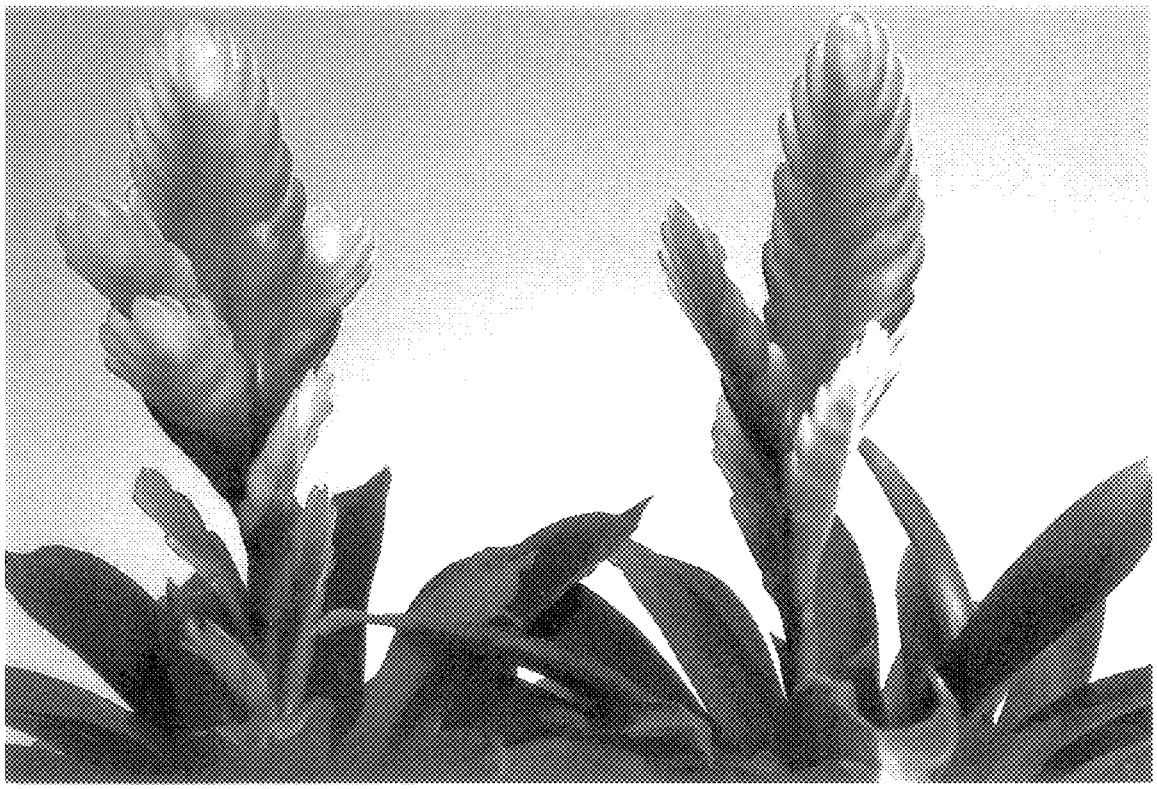

* * * * *